(12) United States Patent
Schlaminger

(10) Patent No.: US 8,379,202 B2
(45) Date of Patent: Feb. 19, 2013

(54) METHOD FOR DETECTING CONTAMINANTS

(75) Inventor: Michael Schlaminger, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 358 days.

(21) Appl. No.: 12/768,077

(22) Filed: Apr. 27, 2010

(65) Prior Publication Data

US 2010/0277727 A1    Nov. 4, 2010

(30) Foreign Application Priority Data

Apr. 30, 2009 (EP) ..................... 09159152

(51) Int. Cl.
*G01J 3/28* (2006.01)

(52) U.S. Cl. ..................... 356/326

(58) Field of Classification Search ........... None
See application file for complete search history.

(56) References Cited

U.S. PATENT DOCUMENTS

| 6,455,852 | B2 * | 9/2002 | Mori et al. ............... 250/339.13 |
| 6,458,213 | B1 | 10/2002 | Krieg et al. |
| 6,687,620 | B1 * | 2/2004 | Haaland et al. ............... 702/22 |

FOREIGN PATENT DOCUMENTS

| EP | 0210417 B1 | 2/1987 |
| EP | 0915338 A2 | 5/1999 |
| WO | 2004070369 A1 | 8/2004 |

* cited by examiner

*Primary Examiner* — Tu Nguyen
(74) *Attorney, Agent, or Firm* — Roche Diagnostics Operations, Inc.

(57) ABSTRACT

A method for the detection of contaminants in an optical measuring cuvette of a spectrophotometer, typically an oximeter for determining hemoglobin derivatives, is provided, in which measuring cuvette, in addition to at least one sample measurement to obtain a sample spectrum $I(\lambda)$, at least one reference measurement is performed using a reference liquid to obtain a reference spectrum $I_0(\lambda)$. The reference spectrum $I_0(\lambda)$ is compared to a known target spectrum $I_{0soll}(\lambda)$, which is associated with the measuring cuvette, comparison parameters being obtained, it being decided automatically whether a contamination of the measuring cuvette exists as a function of predefined threshold values of the comparison parameters.

17 Claims, 6 Drawing Sheets

METHOD FOR DETECTING CONTAMINANTS

BACKGROUND OF THE INVENTION

The invention relates to a method for the detection of contaminants in an optical measuring cuvette of a spectrophotometer, typically an oximeter for determining hemoglobin derivatives, in which measuring cuvette, in addition to at least one sample measurement to obtain a sample spectrum $I(\lambda)$, at least one reference measurement is performed using a reference liquid to obtain a reference spectrum $I_0(\lambda)$.

Spectrophotometers or spectrometers are generally devices for representing a spectrum and offer the capability of recording and analyzing optical spectra. Spectrometers are used widely, inter alia, in chemical and medical analytics, in order to be able to determine components of a liquid on the basis of their spectral properties. Spectrometers used for this purpose frequently operate according to the polychromator principle, i.e., in this method the incident light is first split using a polychromator into its spectral components, which may thus be imaged simultaneously on a detector array, after the passage through the sample liquid provided in the measuring cuvette. In this way, the entire spectrum can be registered simultaneously (Optical Multichannel Analyzer (OMA) or Multi Channel Spectrometer (MCS)). Modern multichannel spectrometers may transmit a complete spectrum very rapidly to the analysis electronics. A typical field of use for spectrometers is, for example, the analytical determination of hemoglobin derivatives in blood, the so-called CO-oximetry. An example of such a spectrometry module is the COOX module of the cobas b 221 (Roche Diagnostics GmbH, Germany) for the determination of bilirubin (Bili), total hemoglobin (tHb), and the hemoglobin derivatives oxyhemoglobin (O2Hb), desoxyhemoglobin (HHb), carboxyhemoglobin (COHb), and methemoglobin (MetHb). The hemoglobin derivatives and bilirubin are determined by spectrophotometry on the basis of the Lambert-Beer law (see equation (1)). The optical system of this CO-oximetry module essentially comprises a halogen lamp, gap, cuvette holder having a measuring cuvette, polychromator, and detection unit. The light of a halogen lamp is conducted to the cuvette holder with the aid of an optical fiber. In the measuring cuvette, the light is partially absorbed by the sample and partially transmitted. The absorption is characteristic of the composition of the sample. The transmitted light is conducted to the polychromator by a further optical fiber, where it is split into its spectral components and imaged on the surface of a photosensitive receiver (CCD sensor). The absorption and finally the concentration of the hemoglobin derivatives are calculated from the electrical signal resulting therefrom. In order to achieve high reliability in operation, the polychromator is calibrated using an installed spectral light source.

As noted above, the concentration calculation of the hemoglobin derivatives is based on the measured summation absorption of the individual components at multiple wavelengths:

$$A_\lambda = \log(I_{0\lambda}/I_\lambda) = \Sigma \epsilon_{i_\lambda} * c_i * d \tag{1}$$

in which:
$\lambda$ wavelength
i ith individual component
A absorption
$I_0$ reference intensity: intensity of the transmitted light of the cuvette filled with water or air
I sample intensity: intensity of the transmitted light of the cuvette filled with a measuring liquid (e.g., blood)
$\epsilon$ extinction coefficient
c concentration
d layer thickness (internal diameter of the cuvette).

Both the measuring liquid and also the reference liquid or the reference medium (e.g., non-absorbing liquid) are measured at staggered times in the same cuvette; i.e., the cuvette must be cleaned and subsequently filled with reference liquid between the two measuring points. A disadvantage of the current measuring method lies precisely therein: if the sample and/or measuring liquid is not completely washed out of the cuvette, or an optically interfering layer forms in the measuring cuvette over time—after multiple measuring cycles each having one sample measurement and at least one reference measurement—it remains unknown. The light of the reference measurement is additionally absorbed by such contaminants, i.e., $I_0$ no longer corresponds to the pure reference spectrum (spectrum of the excitation light source, possibly superimposed with spectral effects of optical system (e.g., filter) and by characteristic absorptions of the uncontaminated cuvette filled with reference solution), but rather is additionally superimposed with the absorption of the contaminant. If these errors remain unrecognized, the absorption A of the sample is incorrectly calculated, which inevitably results in incorrect concentration values.

A method for the spectrophotometric determination of the concentration of a number of hemoglobin derivatives in whole blood is known from EP 0 210 417 B1 in this context, in which the turbidity caused by the blood sample is taken into consideration. The blood sample has a number n of individual wavelengths applied thereto, which is at least equal to the number of the hemoglobin derivatives to be determined plus one, the concentrations being determined on the basis of the absorption values at the individual wavelengths by using sets of predetermined coefficients, which represent the absorption characteristics of the individual hemoglobin derivatives at each of the wavelengths and the absorption characteristics of at least one turbidity component at each of the wavelengths. The concentrations of the hemoglobin derivatives are then calculated on the basis of an equation system using an n×n matrix, the turbidity caused by the whole blood is being treated mathematically like one of the concentrations of the hemoglobin derivatives to be calculated. An application of this method to optically interfering layers in the measuring cuvette, such as deposits of prior blood samples, is unrewarding, however, because the resulting concentration values would not be differentiable from the measured values of a current sample measurement.

Furthermore, methods and devices for monitoring contaminant states of various liquids are also known from other technical fields, which are described, for example, in WO 2004/070369 A1. A method is presented here for determining and/or monitoring contaminant states in liquids, in which a white light LED and at least one injection luminescence diode, which emits infrared or ultraviolet radiation, are used. The method exploits the modification of the emission spectrum of the white LED, changes of the peak wavelengths, the ratios of the peaks of the injection luminescence to the peak of the photoluminescence, the selective absorptions, the excitation to fluorescence, the intensity of the peak wavelengths, and the integral emissions, as well as the comparison of the data to modified spectra being used, which are registered with the aid of a fiber-optic compact spectrometer. This method has the disadvantage of the fact that additional light sources are required and the method is not applicable on typical spectral spectrometers without adaptations.

SUMMARY OF THE INVENTION

It is against the above background that the present invention provides certain unobvious advantages and advancements over the prior art. In particular, the inventor has recognized a need for improvements in methods for the detection of contaminants, typically in an optical measuring cuvette of a spectrophotometer.

Although the present invention is not limited to specific advantages or functionality, it is noted that the present invention allows a statement about the quality (correctness) of a reference measurement to be made without additional apparatus or measuring-technology expenditure, in order to be able to initiate further measures rapidly and optionally automatically in the event of flawed reference measurements.

In accordance with one embodiment of the invention, a method for detecting contaminants in an optical measuring cuvette of a spectrophotometer is provided comprising performing at least one sample measurement in a measuring cuvette to obtain a sample spectrum $I(\lambda)$, performing at least one reference measurement in said measuring cuvette using a reference liquid to obtain a reference spectrum $I_0(\lambda)$, comparing the reference spectrum $I_0(\lambda)$ to a known target spectrum $I_{0soll}(\lambda)$, which is associated with the measuring cuvette, to obtain comparison parameters, and deciding automatically as a function of predefined threshold values of the comparison parameters whether a contamination of the measuring cuvette exists.

These and other features and advantages of the present invention will be more fully understood from the following detailed description of the invention taken together with the accompanying drawings. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

DETAILED DESCRIPTION OF THE INVENTION

The target spectrum $I_{0soll}(\lambda)$ can be ascertained by measuring a known non-contaminated measuring cuvette filled with the reference liquid or with gas, for example, with ambient air. This can be performed, for example, when a new measuring cuvette is inserted into a spectrophotometer for the first time. For this purpose, the spectrum of the air-filled measuring cuvette can be ascertained first and in following steps the spectrum of a measuring cuvette filled with reference liquid can be ascertained.

The target spectrum $I_{0soll}(\lambda)$ is typically obtained from an initial measurement of an unused measuring cuvette, which is newly inserted into the spectrophotometer and filled with the reference liquid.

The target spectrum can also be acquired at the factory during the production of the measuring cuvettes, and fastened in electronic form, for example, as a computer chip, on the measuring cuvette and automatically input by the spectrophotometer.

The target spectrum $I_{0soll}(\lambda)$ can be ascertained from a plurality of individual measurements of multiple optical measuring cuvettes.

According to an embodiment of the invention, a functional liquid of the spectrophotometer, typically a cleaning fluid, which has essentially no absorption in the spectral range employed for the detection of contaminants, is used as the reference liquid.

In the event of the existence of a contaminant of the measuring cuvette, typically after a quantitative evaluation of the contaminant, at least one of the following measures is initiated according to the invention—typically automatically:

repetition of washing steps of the measuring cuvette;
additional washing function, optionally using special washing solutions and washing cycles deviating from the standard cycle;
output of error messages on the spectrophotometer;
correction of the output measured values on the basis of the ascertained incorrect absorption because of the contaminant;
request for a service technician;
blocking of the spectrophotometer for further measurements;
output of recommendations, such as replacement of the measuring cuvette or the cuvette unit.

The method according to the present invention is suitable above all upon the use of reusable cuvettes or flow-through cuvettes, in which a plurality of measurements (for example, of sample solutions, but also of calibration or QC solutions) are performed in chronological sequence.

a) Evaluation of the Contaminant on the Basis of the Curve of the Reference Spectrum:

According to the invention, according to a first variant, the spectral curve shape of the measured reference spectrum $I_0(\lambda)$ can be compared to the spectral curve shape of the target spectrum $I_{0soll}(\lambda)$ and the comparison parameters can preferably be obtained by standardizing the spectral curve shapes. For example, the comparison parameters may be obtained by differential or quotient calculation of the spectral curves.

Figure 1:
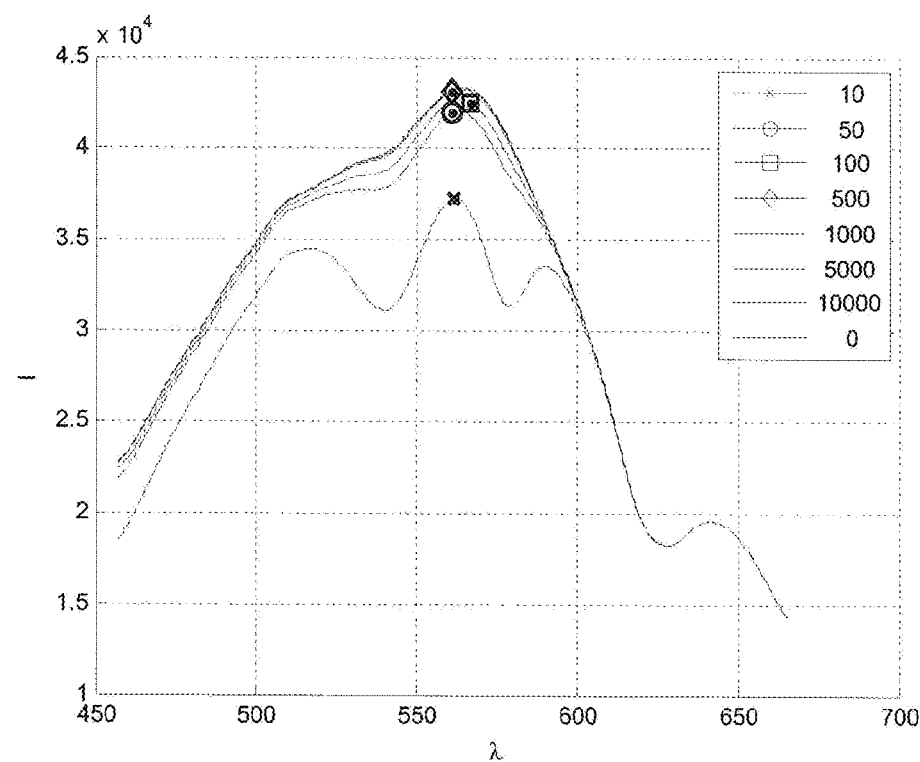
FIG. 1 shows multiple reference spectra $I_0(\lambda)$ of a measuring cuvette in the wavelength range $\lambda$ between 450 nm and 700 nm, in accordance with an embodiment of the present invention, the intensity I being plotted on the ordinate and the degree of contamination 1/x being simulated with the aid of blood samples diluted by the factor x (10 to 10,000)
Figure 2:
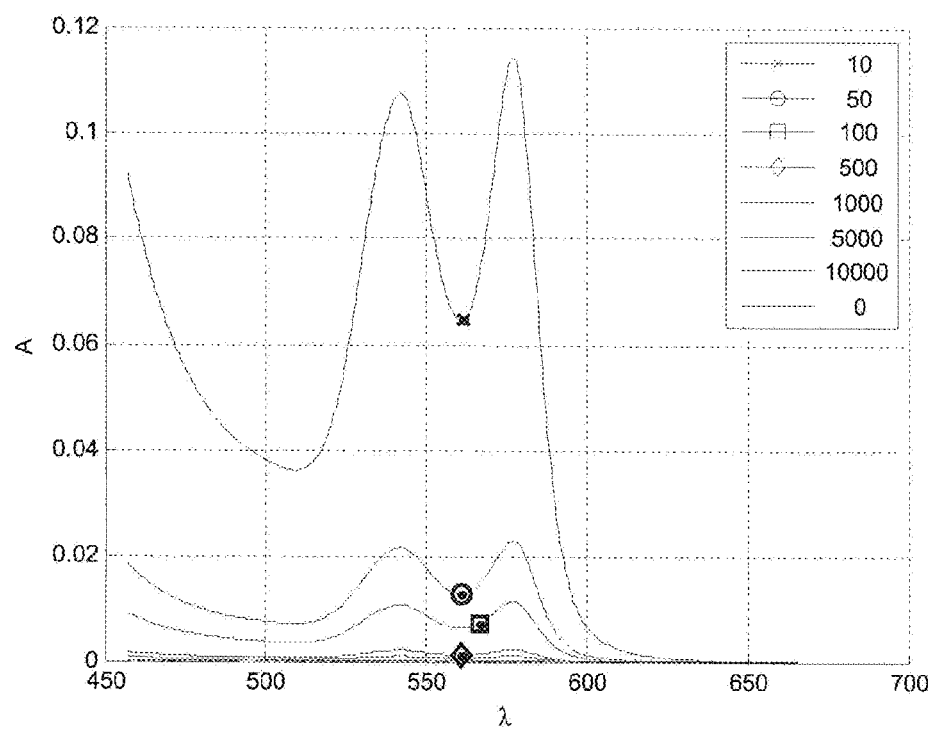
FIG. 2 shows the residual/incorrect absorptions A for the particular degree of contamination (0, 1/10 to 1/10,000) ascertained for the spectra according to FIG. 1, in the wavelength range $\lambda$ between 450 nm and 700 nm.

It can be seen from FIG. 1 and FIG. 2 that the residual or incorrect absorption of these methods is not very sensitive in the event of slight contamination and measuring limits already occur at a degree of contamination of 1/1000 or 1/5000. The outer envelope curve in FIG. 1 shows a target spectrum $I_{0soll}(\lambda)$ of a clean measuring cuvette.

It is to be noted in this context that the sample intensity I and the reference is variable $I_0$ must be known at the measuring moment to ascertain the absorption values for each wavelength, which can cause problems. The system-related changes occurring in the time interval between the determination of $I_0$ and I, such as the drifting of the intensity of the excitation light source, result in changing values of $I_0$ and thus in erroneous absorption values.

As a countermeasure, two reference measurements $I_{01}$ and $I_{02}$ may be performed at precisely defined intervals to determine $I_0$ after each sample measurement. The actual value of the light intensity at the moment of the sample measurement can be approximated for each wavelength on the basis of these reference measurements by linear extrapolation.

Both the extrapolated, drift-corrected value $I_0$, (at the moment $t_0$), and also a raw value $I_{01}, I_{02}, \ldots$ (at the moments $t_1, t_2, \ldots$) may be used to evaluate'the spectral curve.

b) Evaluation of the Contamination using tHb—Thresholding:

According to the invention, according to a further variant the reference spectrum $I_0(\lambda)$, similarly to a sample spectrum $I(\lambda)$, can be subjected to a sample analysis according to a predetermined analysis algorithm of the spectrophotometer, such as a tHb determination in an oximeter, the target spectrum $I_{0soll}(\lambda)$ being used as the reference spectrum and the measured values obtained from the sample analysis, such as the values for individual hemoglobin derivatives or the tHb measured value, being used as the comparison parameters.

As a result, the sum of the individual concentrations (=tHb value) is obtained. The more the tHb value deviates from 0, the greater the proportion of the contamination in the measured reference spectrum.

A contaminated reference spectrum $I_0(\lambda)$ essentially corresponds to a strongly diluted sample measurement. If one calculates the absorption resulting through the contamination using $I_{0mess}$ and the reference variable $I_{0soll}$ according to the Lambert-Beer law $$A = \log(I_{0soll}/I_{0mess}) \quad (2),$$

it can also be calculated using regression. The tHb value thus obtained must be below a threshold value, so that the cuvette is released for the measurement, otherwise the measures described above are automatically initiated.

c) Evaluation of the Contamination Using Pattern Recognition

A particularly advantageous variant of the invention provides that a predefined pattern spectrum $I_p$ is selected, which has at least one typical absorption peak of one or multiple contaminants, the spectral curve of the incorrect absorption caused by the contaminants is determined from the reference spectrum $I_0(\lambda)$ in relation to the target spectrum $I_{0soll}(\lambda)$, the spectral curve of the incorrect absorption is compared to the selected pattern spectrum $I_p$ using folding, preferably using cross-correlation, and the curve shape obtained from the folding is subjected to a weighted evaluation and comparison parameters are obtained therefrom.

Figure 3:
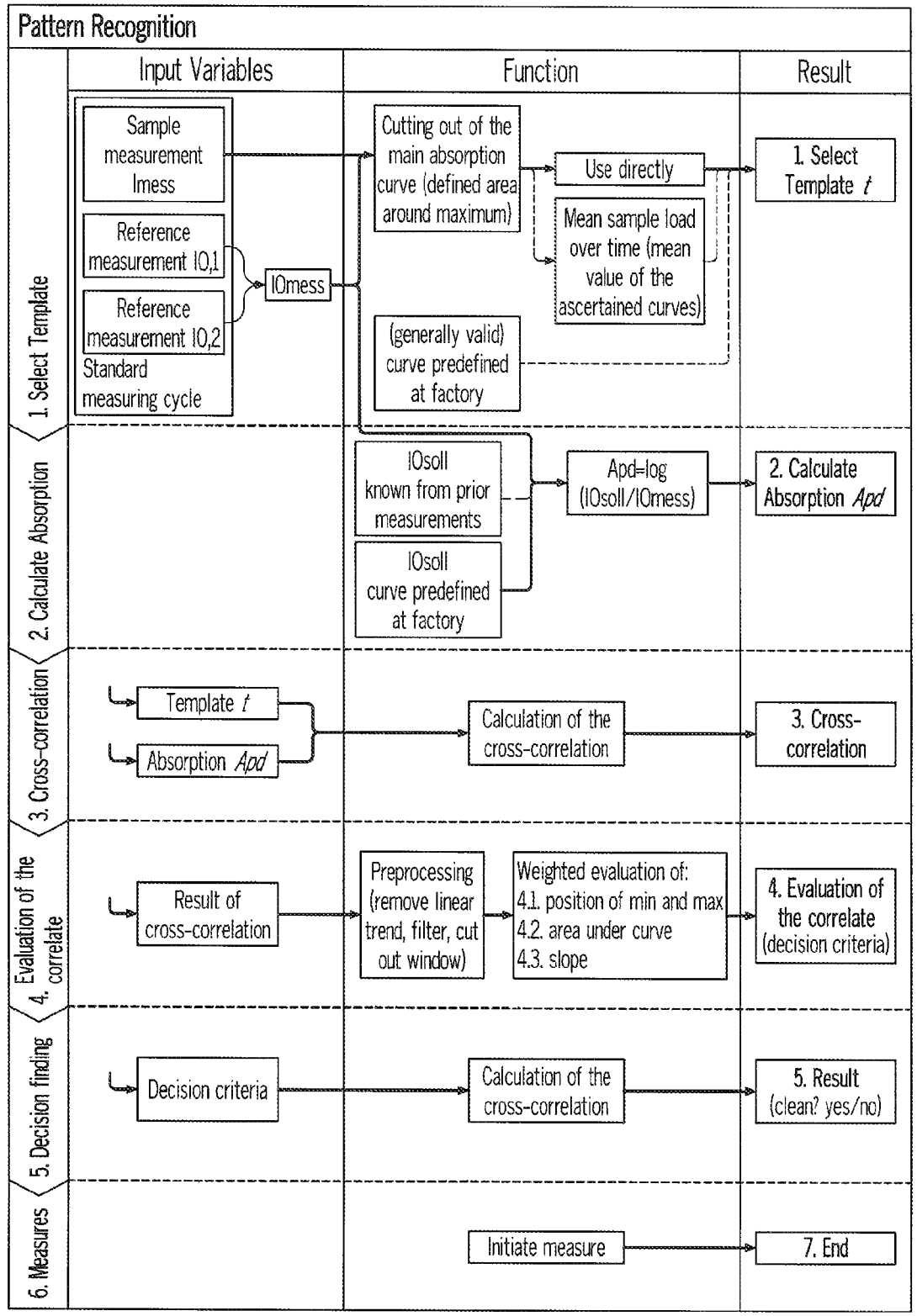
FIG. 3 is a schematic illustration of pattern recognition in accordance with an embodiment of the invention in the form of a flowchart, showing both the standard sequence (solid lines) and also optional sequences (dashed lines)

The methods of the pattern recognition can be divided into five substeps. A schematic illustration in the form of a flowchart is found in FIG. 3, both the standard sequence (solid lines), and also optional sequences (dashed lines) being shown.

In the first step, a curve shape (template) valid for the present optical system is found, which contains the most important features (absorption bands) of possible contaminants. This can be predefined at the factory, or acquired directly or iteratively (via averaging) from the preceding measurement(s). All absorbing substances may be recognized by appropriate definition of the template.

For pattern recognition, the standard collected reference spectra $I_0(\lambda)$ and a target spectrum $I_{0soll}(\lambda)$ valid for the optical system are used. $I_{0soll}(\lambda)$ can again be predefined at the factory, or determined iteratively from prior measurement results. In step 2, the absorption is determined from these two input variables. This curve corresponds to the incorrect absorption resulting through contamination in the reference measurement.

In order to be able to evaluate the curve of the absorption, in the third step, it is compared to the pattern curve selected in step 1 using cross-correlation.

In signal analysis, the cross-correlation function is used to describe the correlation of two signals at different time shifts between the two signals. The following equation applies:

$$R_{xy}(\tau) = \lim_{T_F \to \infty} \frac{1}{T_F} \int_{-T_F/2}^{T_F/2} x(t) \cdot y(t+\tau)\, dt \quad (3)$$

in the present application, cross-correlation is used in the following form, summation being performed over the selected wavelength range $\lambda$min to $\lambda$max:

$$R_{TA}(\lambda) = \Sigma T(\Delta\lambda) * A_{PD}(\lambda + \Delta\lambda) \quad (4)$$

with
$\Delta\lambda$ summed from $\lambda$min to $\lambda$max
R result of the cross-correlation
T template
$A_{PD}$ incorrect absorption by contamination
$\lambda$ current wavelength.

The maximum of the cross-correlation corresponds to the best fit between the template (typical or suspected absorption bands of the contamination) and the incorrect absorption caused by the contamination. The method becomes still more sensitive due to the "online determination" of the template directly from the sample absorption, because the spectral curve of the reference spectrum $I_0(\lambda)$ is deliberately studied after the last sample measurement.

In step 4, evaluation of the curve shape from the cross-correlation (see FIG. 5) is performed after, appropriate pre-processing (removal of linear trends, filtering of noise components in the signal).

Figure 4:
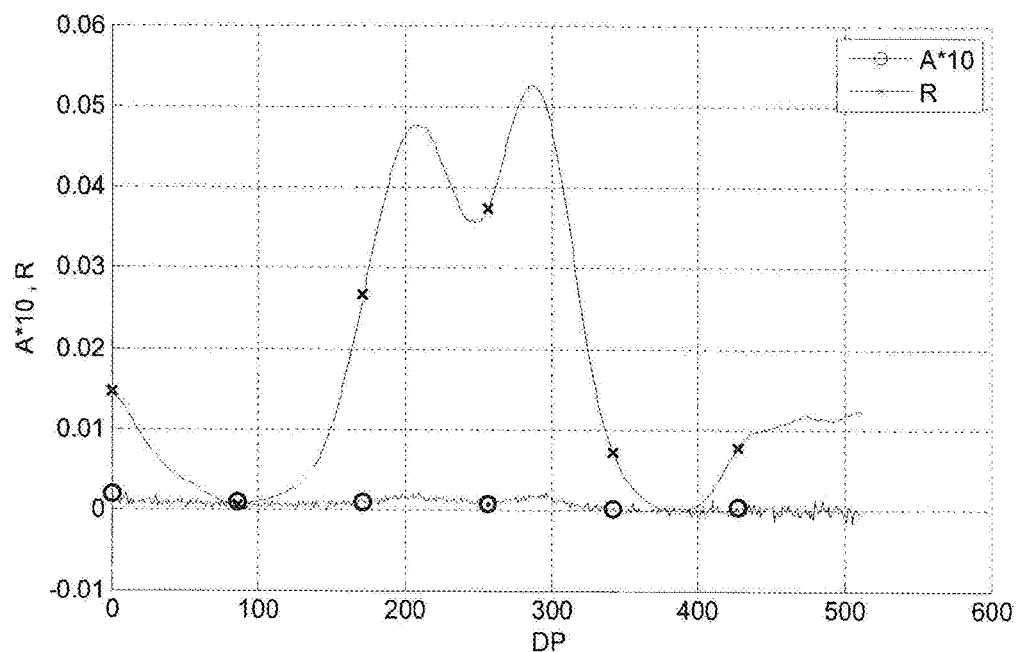
FIG. 4 shows the example of a signal improvement by cross-correlation at a contamination of 1/5000.

FIG. 4 shows the result R of the signal improvement after application of the cross-correlation for a degree of contamination of 1/5000, the original curve of the incorrect Absorption A being designated by "o" and the curve R resulting after the correlation being designated by "x". Data points of the spectrum, which correlate to wavelengths, are plotted as DP values on the x axis of these graphs. Thus, in the case shown in FIG. 4 and FIG. 5, 512 data points are distributed over the wavelength range from approximately 459 nm—approximately 666 nm.

According to another embodiment of the invention, a sub-area of the curve shape which is of interest for measuring technology can be cut out (see "region of interest" shown in bold in FIG. 5), subjected to a weighted evaluation, and the comparison parameters can be obtained therefrom. This method variant is very sensitive, contaminations may thus be established with greater reliability, which correspond to a sample dilution of 1/14,000.

Figure 5:
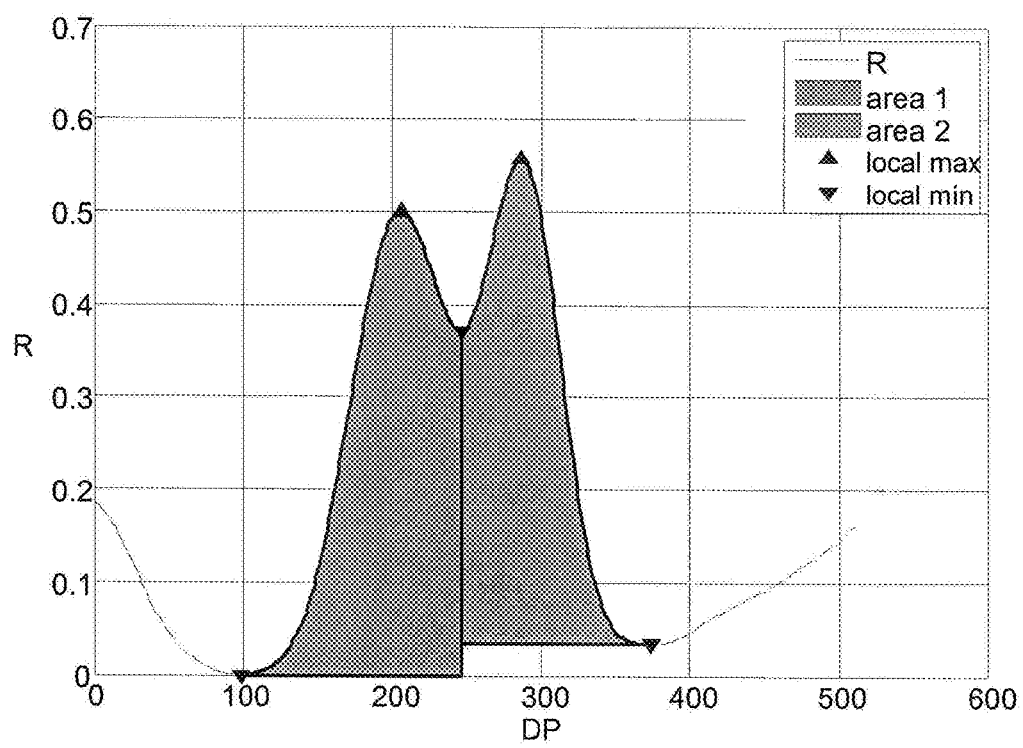
FIG. 5 shows the example of an evaluation of a cross-correlation.

According to yet another embodiment of the invention, for example, the following comparison parameters may be selected and the type and the degree of the contamination may be concluded therefrom:

the positions of minima and maxima within the curve shape obtained by the folding (see FIG. 5);

the areas (areas 1 and 2) below the curve shape obtained by the folding; and/or the slope between selected points of the curve shape obtained by the folding.

The decision about the quality of the reference measurement is made on the basis of these criteria in step 5 and corresponding measures are initiated.

According to the invention, if no contaminant is present or a contaminant to be corrected (for example, by an additional washing procedure) is present in the measuring cuvette according to the criteria listed above, a spectrometric determination of components of a medical sample is performed.

In order that the invention may be more readily understood, reference is made to the following examples, which are intended to illustrate the invention, but not limit the scope thereof.

Examples of Concrete Embodiments of the Invention:

The pattern recognition algorithm was used in the visible range between 459 and 666 nm. A halogen lamp was used as the measuring light source.

For the function check, strongly diluted samples were measured on a spectrophotometer (cobas b 221 from Roche Diagnostics GmbH, Germany). The output sample spectra were then used as the input variable $I_0$ for the method to according to the invention.

Figure 6:
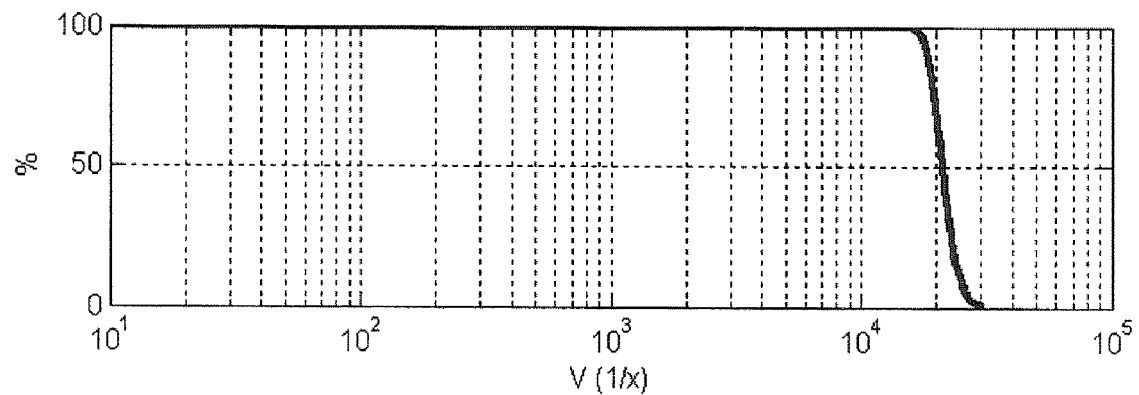
FIGS. 6 and 7 show the result of the simulation measurement.

Simulated data were used for greater dilutions. In this way, the function of the pattern recognition can be detected in a dilution range from $10^{-3}$ to $10^{-5}$. FIG. 6 shows the percentage component of all samples which were recognized as contaminated over a dilution range V(1/x) with $x=10^1$ to $10^5$. Up to a degree of dilution of 1/14000, 100% of all samples were correctly recognized as contaminated, and 90% at a dilution of 1/22000.

Figure 7:
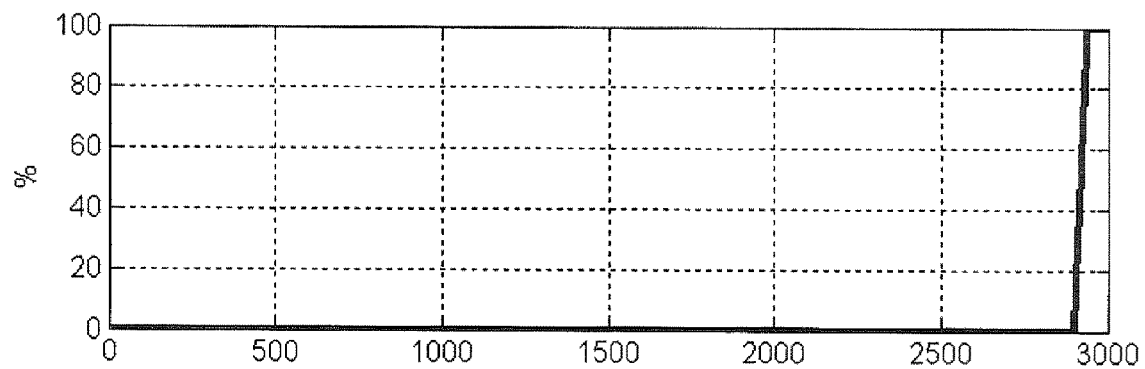

The counter sample according to FIG. 7 did not show any "false positive" results in 10,000 simulated data sets.

EXAMPLE

Finding the Pattern Curve

For weighted amplification of significant absorption patterns, and/or for raising the signal-to-noise ratio by the cross-correlation function (CCF), sufficient a priori knowledge about the form of the pattern to be found in the target signal is advantageous.

It is obvious that ranges of higher absorption have a greater effect in the event of a contamination than ranges of lower absorption. However, this also has the advantage that the curve (typical peak shape) of precisely these areas is more strongly pronounced in the standardized signal. Therefore, precisely these ranges are to be detected during the pattern recognition.

Figure 8:
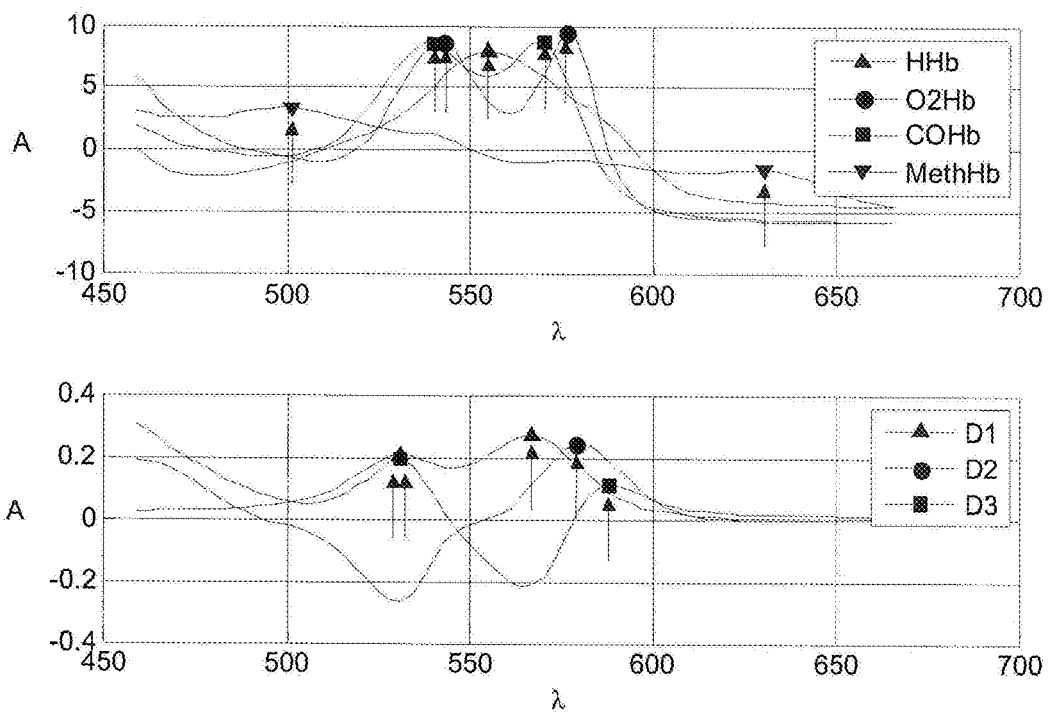
FIG. 8 shows characteristic peaks (absorption peaks) of the hemoglobin derivatives HHb, O2Hb, COHb, and MetHb, or the colorants D1 through D3 of a quality control liquid.

The characteristic peaks of the derivatives (or the various colorants D1 to D3) may be derived from the reference spectrum for a contamination by a blood sample (upper part of the diagram in FIG. 8) or by a calibration or quality control solution (lower part of the diagram in FIG. 8).

With the exception of MetHb, all peaks (for blood, calibration, and QC solution) lie in the center of the spectrum (520 nm<$\lambda$<580 nm) and stand out clearly from the remaining spectrum. In order to be able to use the peaks thus defined for cross-correlation, they must be cut out (masked), two possibilities being considered here:

Method 1:

"Detection by Thresholding the Derivative"

The pattern curve (template) is determined directly from the reference spectra, and/or from the prior measurement. This has the advantage that the template corresponds completely with the pattern to be found, whereby the sensitivity for this one special pattern is increased. If one assumes that a contamination is caused by a prior measurement, this method is reliably optimal.

Figure 9:
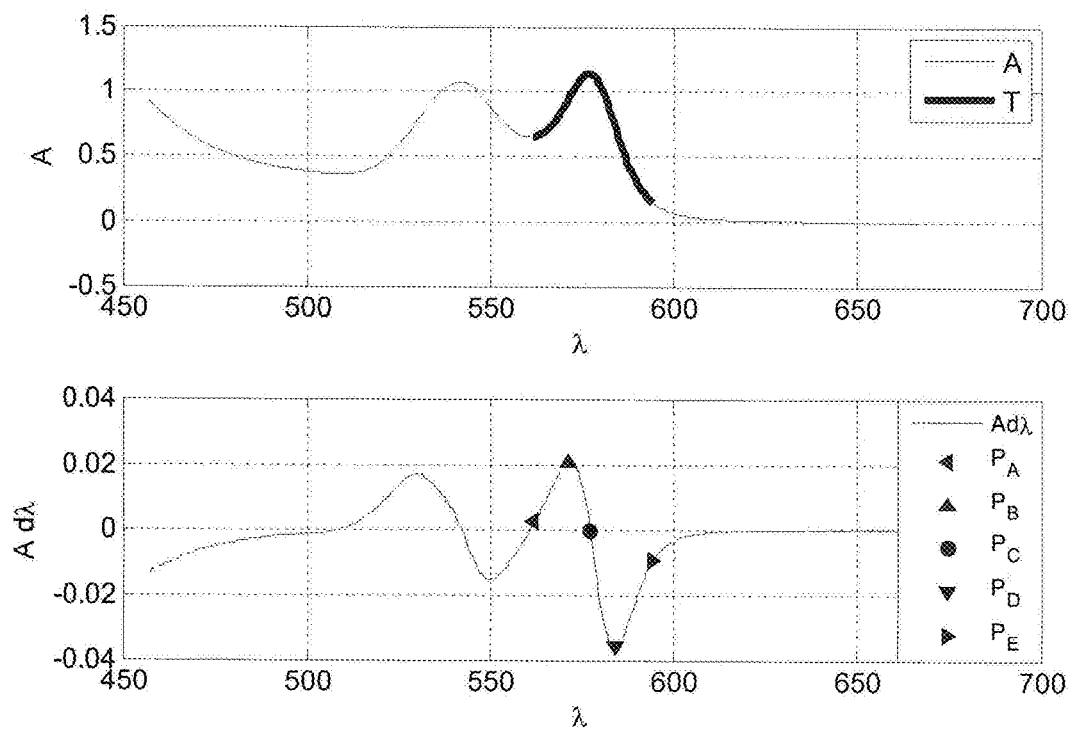
FIG. 9 shows the cutting of the pattern curve (template) out of the measured absorption curve with the aid of the first derivative of the absorption curve.

To cut out the template, the procedure according to FIG. 9 can be used, in the upper part of the graph the absorption curve A having found template T (shown in bold) being shown and in the lower part of the graph, the first derivative $Ad\lambda$ of the curve shape being shown (point $P_C$: maximum of the absorption curve, point $P_B/P_D$: maximum/minimum around $P_C$, point $P_A/P_E$: left/right end value for template):

start at the maximum in the spectrum (zero crossing in the derivative, point $P_C$);

search for the maximum in the derivative in the direction of the beginning (point PB);

search for the minimum in the derivative in the direction of the end (point $P_D$);

from this position, go right/left until the found value falls below a specific fraction of the maximum value (point $P_A$, $P_E$).

By adaptation of the threshold values, the found curve (start and end values, left or right movement on the target function) can be optimized for this specific application.

Figure 10:
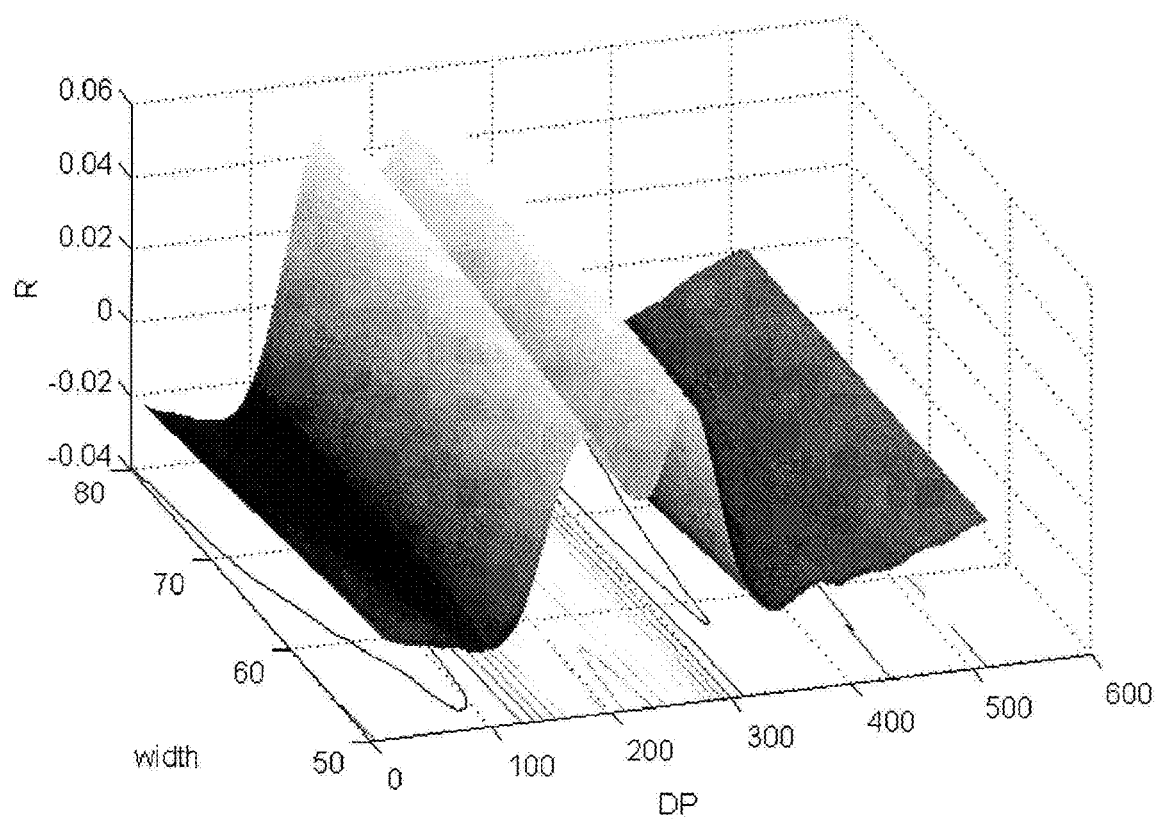
FIG. 10 shows the result of a cross-correlation in a three-dimensional graph.

In FIG. 10, a reference measurement $I_0(\lambda)$ using a blood measurement with native derivative distribution and moderate tHb contamination, which is standardized to a target spectrum $ThbI_{0soll}(\lambda)$, is cross-correlated with the template T found according to the method defined above. (Result R of the CCF: first input signal=contamination (moderate tHb, c native, n=6000), second input signal=cut out template, variation of the curve shape via threshold variation).

The signal-to-noise ratio can be significantly increased and the curve of the absorption causing it can be found again by the cross-correlation. The variation of the curve shape of the template via the threshold value adaptation only has slight effects on the result of the CCF. Slight tilting of the maxima of the CCF (ratio peak1 to peak2) and a rise of the absolute value are shown, which can be explained by the increasing number of data points in the template, however (sum becomes greater in each point).

Method 2

"Approximation of the Template via Parabola"

It is assumed that all significant peaks of a contaminated absorption may be approximated by corresponding adaptation of the polynomial coefficient via a parabola.

The quadratic function (second-order polynomial) for describing a parabola function reads:

$$y=a_2x^2+a_1x+a_0 \quad (5)$$

In order to find the optimum parabola shape, the coefficients $a_1$ and $a_0$ may be neglected. Because the parabola must be open downward, $a_2$ must therefore assumed to be negative. To optimize the opening angle (~width), the number of the data points (DP) used for the calculation is varied. Negative values may be suppressed by addition of the minimum of the function. For better comparability, the values thus ascertained are standardized to the maximum of the curve.

The goal is to find a mean between the deviation of the signal and the sensitivity of the CCF, the following being shown: the greater the number of the data points used (width), the higher the achieved deviation, but the lower the sensitivity of the cross-correlation function, as well. The more sensitive the system, the better known patterns are amplified (and vice versa).

If one compares methods 1 and 2, the following conclusion is reached: By cutting the pattern curve T directly out of the reference spectra, and/or out of prior measurements in time, a somewhat greater deviation is achieved at comparable sensitivity (the peaks to be amplified stand out clearly), than with the approximation of the pattern via a parabola, which only applies for one specific case (namely that described by the template T). If both methods are applied to independent spectra, the maxima of the CCF approximately correspond.

Because the absorption used for cutting out the template is noisy, the template per se also has a corresponding noise component, which has an influence which is not negligible on the result of the CCF upon the cross-correlation with the target signal. The noise of the quadratic function (parabola), however, is zero, whereby the noise component of $R_{xy}$ is also minimized.

It is noted that terms like "preferably", "commonly", and "typically" are not utilized herein to limit the scope of the claimed invention or to imply that certain features are critical, essential or even important to the structure or function of the claimed invention. Rather, these terms are merely intended to highlight alternative or additional features that may or may not be utilized in a particular embodiment of the present invention.

Having described the invention in detail and by reference to specific embodiments thereof, it will be apparent that modifications and variations are possible without departing from the scope of the invention defined by the appended claims. More specifically, although some aspects of the present invention are identified herein as preferred or particularly advantageous, it is contemplated that the preset invention is not necessarily limited to these preferred aspects of the invention.

What is claimed is:

1. A method for detecting contaminants in an optical measuring cuvette of a spectrophotometer comprising:
   performing at least one sample measurement in a measuring cuvette to obtain a sample spectrum $I(\lambda)$,
   performing at least one reference measurement in said measuring cuvette using a reference liquid to obtain a reference spectrum $I_0(\lambda)$,
   comparing the reference spectrum $I_0(\lambda)$ to a known target spectrum $I_{0soll}(\lambda)$, which is associated with the measuring cuvette, to obtain comparison parameters, and
   deciding automatically as a function of predefined threshold values of the comparison parameters whether a contamination of the measuring cuvette exists,
   wherein a predefined pattern spectrum $I_p$ is selected, which has at least one typical absorption peak of one or more contaminants, the spectral curve of the incorrect absorption caused by the contaminants from the reference spectrum $I_0(\lambda)$ in relation to the target spectrum $I_{0soll}(\lambda)$ is determined, the spectral curve of the incorrect absorption is compared to the selected pattern spectrum $I_p$ using folding, and the curve shape obtained from the folding is subjected to a weighted evaluation and comparison parameters are obtained therefrom.

2. The method according to claim 1, wherein said spectrophotometer is an oximeter for determining hemoglobin derivatives.

3. The method according to claim 1, wherein the target spectrum $I_{0soll}(\lambda)$ is obtained by measuring a measuring cuvette, which is known to be uncontaminated and is filled with the reference liquid.

4. The method according to claim 1, wherein the target spectrum $I_{0soll}(\lambda)$ is obtained from an initial measurement of an unused measuring cuvette, which is newly inserted into the spectrophotometer and is filled with the reference liquid.

5. The method according to claim 1, wherein the target spectrum $I_{0soll}(\lambda)$ is averaged from a plurality of individual measurements.

6. The method according to claim 1, wherein a functional liquid of the spectrophotometer is used as the reference liquid, which functional liquid is essentially non-absorbent in a spectral range used for detecting contaminants.

7. The method according to claim 6, wherein the functional liquid is a cleaning liquid for said spectrophotometer.

8. The method according to claim 1, wherein the spectral curve shape of the measured reference spectrum $I_0(\lambda)$ is compared to the spectral curve shape of the target spectrum $I_{0soll}(\lambda)$.

9. The method according to claim 8, wherein the comparison parameters are obtained by standardizing the spectral curve shapes.

10. The method according to claim 8, wherein the comparison parameters are obtained by differential or quotient calculation of the spectral curve shapes.

11. The method according to claim 1, wherein the spectral curve of the incorrect absorption is compared to the selected pattern spectrum $I_p$ using cross-correlation.

12. The method according to claim 1, wherein only a sub-area of the curve shape of interest in measuring technology is subjected to a weighted evaluation and comparison parameters are obtained therefrom.

13. The method according to claim 1, wherein the positions of minima and maxima within the curve shape obtained by the folding are selected as the comparison parameters and the type and the degree of the contamination are concluded therefrom.

14. The method according to claim 1, wherein the area under the curve shape obtained by the folding is selected as the comparison parameter and the type and the degree of the contamination are concluded therefrom.

15. The method according to claim 1, wherein the slope between selected points of the curve shape obtained by the folding is selected as the comparison parameter and the type and the degree of the contamination are concluded therefrom.

16. The method according to claim 1, wherein if a contamination of the measuring cuvette is detected, initiating at least one additional action selected from repetition of washing steps of the measuring cuvette; an additional washing function optionally having special washing solutions and washing cycles deviating from the standard cycle; outputting of one or more error messages on the spectrophotometer; correcting the output measured values on the basis of the ascertained incorrect absorption because of the contamination; requesting a service technician; blocking of the spectrophotometer for further measurement; and outputting suggestions, such as replacement of the measuring cuvette or the cuvette unit.

17. A method for the spectrometric determination of components of a medical sample, comprising deciding automatically whether a contamination of an optical measuring cuvette exists according to claim 1, and if there is no contamination or a contamination to be corrected, performing a spectrometric determination of components of a medical sample in the measuring cuvette.

* * * * *